United States Patent [19]

Poncy et al.

[11] 4,020,841

[45] May 3, 1977

[54] CATAMENIAL TAMPON

[76] Inventors: Richard P. Poncy; Mark P. Poncy; George W. Poncy, Sr.; George W. Poncy, Jr.; Robert C. Brandriff, all of 3670 E. Indus. Way., Riviera Beach, Fla. 33404

[22] Filed: June 17, 1975

[21] Appl. No.: 587,676

[52] U.S. Cl. .............................. 128/285; 128/270
[51] Int. Cl.² ........................................ A61F 13/20
[58] Field of Search .......... 128/285, 270, 263, 287; 19/144.5

[56] References Cited

UNITED STATES PATENTS

| | | | |
|---|---|---|---|
| 2,710,007 | 6/1955 | Greiner et al. ................ | 128/285 X |
| 2,998,010 | 8/1961 | Griswold et al. .................. | 128/285 |
| 3,491,758 | 1/1970 | Mullan .................................. | 128/270 |
| 3,523,535 | 8/1970 | Croon et al. ....................... | 128/285 |
| 3,559,646 | 2/1971 | Mullan .............................. | 128/285 |
| 3,805,790 | 4/1974 | Kaczmarzyk et al. ......... | 128/290 R |
| 3,901,240 | 8/1975 | Hoey .......................... | 128/290 R X |

*Primary Examiner*—Robert W. Michell
*Assistant Examiner*—Henry S. Layton
*Attorney, Agent, or Firm*—Lane, Aitken, Dunner & Ziems

[57] ABSTRACT

A catamenial tampon comprising an elongated core of conventional highly absorbent fibrous material enclosed along its sides and posterior ends by a sheath of non-absorbent, resilient and thus compressible foam material whereby the storage capacity of the absorbent core is unaffected by compressive forces due to muscular activity or withdrawal of the tampon, such compression being accommodated fully by said non-absorbent outer sheath.

9 Claims, 4 Drawing Figures

CATAMENIAL TAMPON

BACKGROUND OF THE INVENTION

This invention relates to fluid receptors for use within cavities of the human body and more particularly, it concerns improvements in intravaginal catamenial tampons.

Intravaginal tampons are in common use by women for the retention of fluids or menses discharged along the walls of the vagina during the menstrual cycle. Such tampons are usually formed of absorbent materials such as cotton, rayon cellulose wading, synthetic sponge, cellulose fluff, synthetic fibers or combinations of these materials and compressed or molded usually to a generally cylindrical configuration of a size to fit within the vaginal tract.

Several problems are associated with the use of intravaginal tampons for the collection and retention of menstrual fluids. For example, the peripheral interior contour of the vaginal wall, being unpredictably irregular as compared with the preformed tampon, often leads to the by-pass of fluid menses through the occasional spaces encountered between the outer surface of the tampon and the inner vaginal wall. If the tampon itself is sufficiently flexible or compressible to conform with the peripheral configuration of the vaginal tract, the compressibility of the tampon itself reduces the effectiveness of the tampon to retain or store the menstrual fluids. In particular, compression of the tampon will result in the discharge of accumulated fluids both when the tampon is compressed directly such as during withdrawal or indirectly due to the increase in intravaginal pressure caused by the most common of body movements. Further, the use of tampons is commonly accompanied with undesirable irritation as a result of frequent insertion and withdrawal during periods of heavy menses flow. Chafing may occur also during periods of light menses flow because of the tendency of the tampon to absorb whatever small amount of liquids are present on the vaginal walls thereby to generate excess friction between the tampon and the vaginal walls.

SUMMARY OF THE PRESENT INVENTION

In accordance with the present invention, the difficulties heretofore experienced with intravaginal catamenial tampons are substantially alleviated by assembling a conventional, essentially non-compressible, fibrous tampon as an exposed core in a cup-like vessel or sheath of closed-celled, non-absorbent, resilient foam such as polyurethane. The tampon assembly thus provided may be positioned in the vaginal tract so that the tampon core is exposed at the upper end to the flow of menstrual fluids directed inwardly over the upper edges of the foam sheath. The foam sheath or vessel in the assembly thus functions not only as a compressible seal by which leakage of the menstrual fluids between the tampon and the walls of the vaginal tract is inhibited but also and perhaps more importantly as a cushion by which fluid expelling compression of the fibrous core is avoided both during use as a result of muscular activity and during withdrawal of the tampon from the vagina.

Accordingly, among the objects of the present invention are: the provision of a improved tampon particularly suited for intravaginal use; the provision of such a tampon by which the storage capacity for menstrual fluids is significantly increased over tampons of the prior art; the provision of such an improved intravaginal tampon in which the capacity for retention of menstrual fluids is unaffected by compression whether such compression is as a result of removal of the tampon or as a result of muscular activity causing a contraction of the vaginal cavity; and the provision of such an intravaginal tampon which is easily inserted and withdrawn, non-irritating in use and highly effective in its capacity for storage of menstrual fluids.

Other objects and further scope of applicability of the present invention will become apparent from the detailed description to follow taken in conjunction with the accompanying drawings in which like parts are designated by like reference numerals.

DETAILED DESCRIPTION OF THE PREFERRED EMBODIMENT

Figure 1:
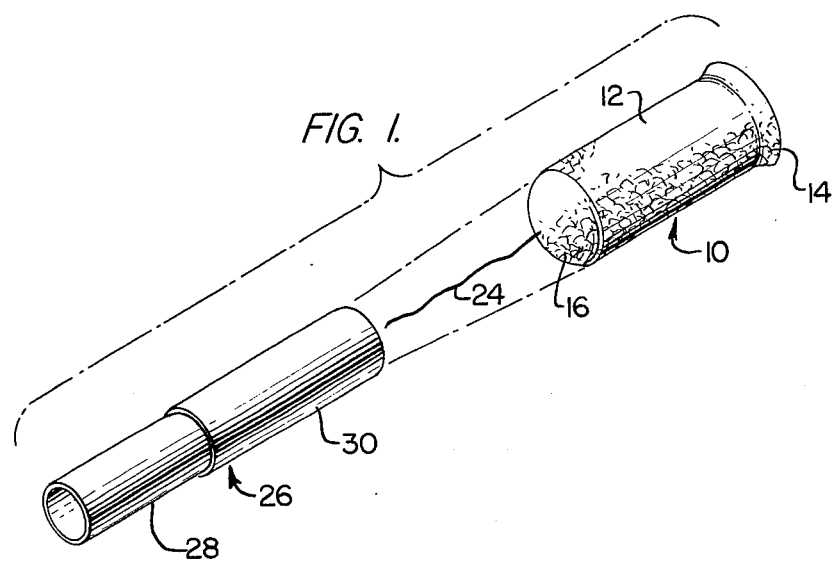
FIG. 1 is a exploded perspective view illustrating the relation of the improved tampon of this invention with respect to a telescopic applicator.
Figure 2:
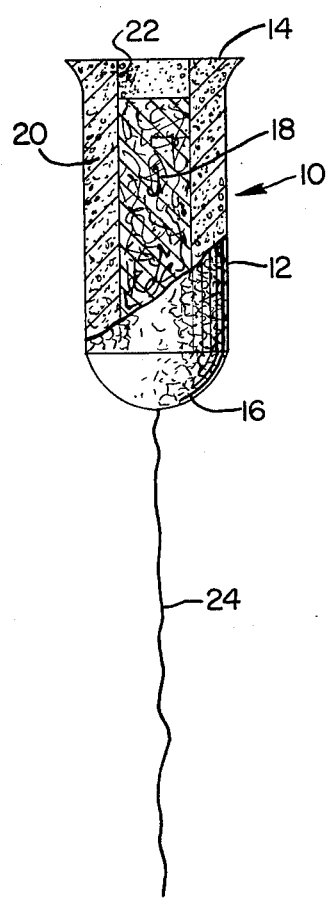
FIG. 2 is an elevation of the tampon in partial cross-section.

In FIGS. 1 and 2 of the drawing, the improved tampon of the present invention is generally designated by the reference numeral 10 and shown in its relaxed or initial condition to establish an essentially cylindrical body 12 having an outwardly flared frontal or upper end 14 and a lower or posterior end 16 of essentially hemispherical configuration. The interior construction of the tampon 10 is shown in FIG. 2 to include a central core 18 of relatively non-compressible, absorbent fibrous material enclosed along its side and posterior ends by a sheath of non-absorbent resilient foam 20. Although the foam sheath extends about the posterior end 16 of the core 18, the frontal end 14 is formed with an opening 22 coextensive with the core to effect a cup-like vessel conformation in the sheath 20.

Figure 3:
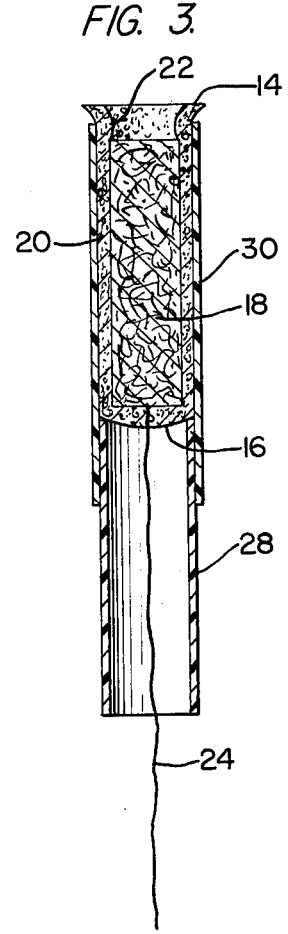
FIG. 3 is a vertical section of the tampon disposed in the telescopic applicator shown in FIG. 1 prior to insertion.

A removal cord 24 is anchored in the core 18 and extends through the lower end 16 of the sheath 20 to be accessible for removal of the tampon 10 after use. The tampon 10 also is adapted to be inserted using a conventional applicator 26 as shown in FIGS. 1 and 3 which includes inner and outer telescopic tubes 28 and 30, respectively of cardboard or other suitable material conventionally employed for the insertion of catamenial tampons. It will be noted from FIG. 3 of the drawings that the outwardly flared configuration at the frontal end 14 of the sheath provides a protective cushion partially about the insertion end of the tube 30.

As above indicated, the core 18 is highly absorbent and relatively non-compressible particularly in relation to the compressibility of the resilient sheath 20. Although the specific structure of the core 18, in itself, or the material from which it is formed may vary, a preferred core for tampons of the invention intended for use by normal adult women is provided by a conventional tampon available commercially under the trademark "Junior Tampax" and manufactured by Tampax, Incorporated. The construction of such absorbent devices is fully disclosed in U.S. Pat. No. 3,371,666 issued Mar. 5, 1968 to Albert W. Lewing and accordingly, the disclosure of that patent is incorporated herein by reference. The absorbent core construction illustrated in the aforementioned patent has been found desirable because changes in its configuration with the absorption of menstrual fluid is resolved solely in elongation, there being relatively no variation in its cross section or diameter with use.

Figure 4:
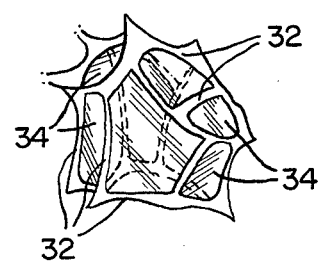
FIG. 4 is a greatly enlarged view depicting the cell construction of the resilient foam employed in the tampon of this invention.

An important aspect of the present invention is that the outer sheath 20 completely accommodates any compression of the overall tampon 10 without an attendant discharge of fluid therefrom. For this reason, the sheath 20 is formed of a non-absorbent compessible foam such as closed celled polyurethane. Although materials other than polyurethane may be used in accordance with the invention, it is important only that the material be easily compressible and non-absorbent. The cellular construction of closed celled polyurethane is illustrated in FIG. 4 of the drawings to include generally a resilient skeletal structure 32 supporting closed cell membranes 34. An added measure of non-absorption without compromise of the resilient qualities of the polyurethane may be achieved by a closed cell polyurethane impregnated with polyvinyl chloride. Various other foam materials having similar characteristics and which are well known to those skilled in the foam art may be used wthout changing the characteristics of the tampon 10. It is contemplated further that the thickness of the sheath 20 be on the order of one-quarter inch to provide an overall diameter of the tampon body 12 of seven-eighths of an inch in its relaxed condition.

In use, the tampon is inserted with the applicator 26 in conventional fashion to expose the frontal end to the flow of the menstrual fluids in the vaginal tract. Because of the opening 22 in the frontal end 14 and the exposure of the highly absorbent core 18 at the opening 22, the fluids will be directed inwardly by the sheath 20 to be absorbed and stored in the core 18. The sheath not only functions as in the nature of a compressible seal about the absorbent core 18 but isolates the core from compressive forces caused for example, by muscular activity and especially during withdrawal of the tampon using the cord 24 so that the storage capacity for menstrual fluids absorbed in the core is unaffected by such compression. Because the sheath 20 is formed of non-absorbent material, it will retain no fluids to be discharged upon such compression.

Thus it will be seen that by this invention there is provided an improved catamenial tampon by which the above mentioned objectives are completely fulfilled. Since modifications and/or changes are contemplated in the disclosed embodiment it is expressly intended that the foregoing description is illustrative of a preferred embodiment only, not limiting, and that the true spirit and scope of the present invention be determined by reference to the appended claims.

We claim:
1. A catamenial tampon comprising:
   an elongated core of relatively non-compressible, highly absorbent fibrous material; and
   an outer sheath of non-absorbent, resilient closed cell foam enclosing said core along the sides and at one end thereof, said core being exposed only at the opposite end from said one end through a opening in said sheath;
   the outer sheath having an exterior configuration and size to fit within the human vagina.
2. The tampon recited in claim 1 in which the exterior configuration of said sheath is established by a cylindrical body portion having a hemispherical shape at said one end of said core and an outwardly flared shape at said other end of said core.
3. The tampon recited in claim 1 including a withdrawal cord extending from said core through said sheath at said one end of said core.
4. The tampon recited in claim 1 in which said core expands longitudinally upon absorption of fluids and is relatively unaltered in cross-sectional dimension by the absorption of such fluids.
5. The tampon recited in claim 1 wherein the radial thickness of said sheath along the side walls of said core is approximately one-quarter inch and wherein the overall transverse width of said tampon is on the order of seven-eighths of a inch.
6. The tampon recited in claim 1 wherein said sheath is formed of a closed celled polyurethane foam.
7. The tampon recited in claim 6 wherein said polyurethane foam is impregnated with polyvinyl chloride.
8. The tampon recited in claim 1, further comprising an applicator tube surrounding said sheath, the insertion end of said sheath extending axially beyond the insertion end of said applicator tube and being enlarged to extend radially beyond the outer dimension of said tube to provide a protective cushion about the insertion end of said tube.
9. A catamenial tampon comprising:
   an absorbent core;
   an outer sheath of non-absorbent, closed cell, resilient foam surrounding said core;
   an applicator tube surrounding said sheath;
   the insertion end of said sheath extending axially beyond the insertion end of said tube and being enlarged to extend radially beyond the outer dimension of the insertion end of said tube to provide a protective cushion about the insertion end of said tube.

* * * * *